United States Patent [19]

Tekulve

[11] Patent Number: 5,797,953
[45] Date of Patent: Aug. 25, 1998

[54] HELICAL EMBOLIZATION COIL

[75] Inventor: Kurt J. Tekulve, Ellettsville, Ind.

[73] Assignee: Cook Incorporated, Bloomington, Ind.

[21] Appl. No.: 609,767

[22] Filed: Feb. 23, 1996

Related U.S. Application Data

[63] Continuation of Ser. No. 507,600, Jul. 26, 1995, abandoned, which is a continuation of Ser. No. 210,798, Mar. 18, 1994, abandoned.

[51] Int. Cl.$^6$ .................................................. A61B 17/00
[52] U.S. Cl. .................................................. 606/200; 623/1
[58] Field of Search ............................ 606/191, 194, 606/195, 198, 200; 623/1, 12; 128/899

[56] References Cited

U.S. PATENT DOCUMENTS

| | | |
|---|---|---|
| 4,706,671 | 11/1987 | Weinrib . |
| 4,994,069 | 2/1991 | Ritchart et al. . |
| 5,108,407 | 4/1992 | Geremia et al. . |
| 5,108,420 | 4/1992 | Marks . |
| 5,122,136 | 6/1992 | Guglielmi et al. . |
| 5,133,709 | 7/1992 | Prince . |
| 5,133,731 | 7/1992 | Butler et al. . |
| 5,167,624 | 12/1992 | Butler et al. . |
| 5,190,546 | 3/1993 | Jervis . |
| 5,192,301 | 3/1993 | Kamiya et al. . |
| 5,217,484 | 6/1993 | Marks . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,267,955 | 12/1993 | Hanson . |

FOREIGN PATENT DOCUMENTS

| | | |
|---|---|---|
| 3203410 | 11/1982 | Germany . |
| 1771719 | 10/1992 | U.S.S.R. . |
| 9216163 | 10/1992 | WIPO . |
| 9407560 | 4/1994 | WIPO . |
| 9409705 | 5/1994 | WIPO . |

OTHER PUBLICATIONS

Cook Incorporated, "Embolization Coils," Bloomington, Indiana, 1988.
Cragg, Andrew et al., "A New Percutaneous Vena Cave Filter", AJR Sep. 1983.

Primary Examiner—Michael Powell Buiz
Assistant Examiner—William Lewis
Attorney, Agent, or Firm—Richard J. Godlewski

[57] ABSTRACT

A conically helically shaped embolization coil (10) for occluding a blood vessel, aneurysm, and the like. The embolization coil includes a continuous platinum-tungsten alloy wire strand (11) wound into a longitudinally extending coil (12) having a plurality of tightly spaced turns (13). The longitudinally extending coil is wound into a conically helically shaped coil (15) with a plurality of radially expanding turns (16) that has spacing that increases proximally from the distal end (29) of the coil. Distal turn (17) of the radially expanding turns has a minor diameter (18) less than a minimum diameter (34) of a vessel (32) of which the embolization is to be positioned therein. Uncompressed proximal turn (19) of the radially expanding turns has a major diameter (20) greater than a maximum diameter (33) of the vessel in which the coil to be positioned. The conically helically shaped coil and particular diameter ensure that the coil is precisely positioned in a vessel lumen without longitudinal displacement of the delivery catheter. The coil is stress relieved and, in particular, heat treated by heating the coil to a stress relief temperature of the continuous wire strand and cooled to relieve residual stresses formed during the winding of the coil and to minimize the formation of new residual stresses formed during the cool down period of the heat treatment. Thrombogenic fibers (26) are positioned in the tightly spaced turns of the coil to attract thrombus and build up a mass that occludes the vessel lumen.

19 Claims, 3 Drawing Sheets

HELICAL EMBOLIZATION COIL

RELATED APPLICATIONS

This is a continuation of application Ser. No. 08/507,600, filed Jul. 26, 1995, now abandoned which is a file wrapper continuation of application Ser. No. 08/210,798, filed Mar. 18, 1994, now abandoned.

TECHNICAL FIELD

This invention relates generally to embolization coils and, in particular, to an embolization coil that is conically helically shaped.

BACKGROUND OF THE INVENTION

Intravascular interventional procedures for providing an artificial embolism are desirable in some patients for controlling internal bleeding, preventing blood supply to tumors, or relieving pressure in the vessel wall near an aneurysm. Several approaches are known for providing an artificial embolism, including the use of an inflatable, detachable balloon or the injection of a coagulative substance. Another approach utilizes an occlusive wire coil and delivery system for positioning the coil at a desirable site in a blood vessel.

One wire coil and delivery system includes a flexible, coiled wire that when released from the distal end of a delivery catheter assumes a randomly coiled, space-filling mass. The wire is released from the catheter by a pusher catheter with a closed distal end for engaging the proximal end of the coil. A problem with this system is that the wire coil is just pushed out the distal end of the delivery catheter toward the target embolism site and then assumes a folded, convoluted configuration. This folded, convoluted configuration is obtained with the use of an occlusion wire that possesses memory which returns the wire from a stretched to a relaxed convoluted condition. One problem with this convoluted configuration coil is that precise positioning of the coil at the occlusion site is difficult to obtain. This is mainly due to the coiled configuration of the wire in which the distal end of the convoluted wire engages the wall of the vessel and longitudinally displaces the delivery catheter. As a result, the delivery catheter and occlusion coil are proximally displaced from the desired occlusion site. Such longitudinal displacement can readily prevent an aneurysm from being occluded. Furthermore, the displaced convoluted coil, which is to be positioned in, for example, an aneurysm, then proceeds downstream and causes an occlusion at an undesired site. This can cause additional pressure to be applied to the already weakened wall of the aneurysm.

Another problem with this convoluted coil is ensuring that sufficient mass is positioned across the cross-sectional area of the vessel lumen to sufficiently restrict blood flow.

SUMMARY OF THE INVENTION

The foregoing problems are solved and a technical advance is achieved in an illustrative embolization coil that is conically helically shaped with a plurality of radially expanding turns. The distal turn of the radially expanding turns has a minor diameter less than the minimum diameter of a vessel in which the embolization coil is to be positioned. This advantageously allows for precise positioning of the coil at the embolization site. The distal end of the coil is introduced from a delivery catheter into the central region of the vessel without longitudinally displacing the delivery catheter from the occlusion site. As the proximal radially increasing turns of the coil expand against the interior surface of the vessel wall, the embolization coil is fixedly positioned in the vessel with the longitudinal axis of the coil being substantially aligned with that of the vessel lumen. The uncompressed proximal turn of the coil has a major diameter greater than the maximum diameter of the vessel to advantageously expand against the interior surface of the vessel wall. As a result, the conically helically shaped coil is fixedly and precisely positioned in the vessel at the occlusion site. Furthermore, the radially expanding coil turns effectively covers the cross-sectional area of the vessel lumen, thus significantly reducing blood flow through the coil.

To further occlude the vessel, the embolization coil includes a continuous wire strand that is wound into a longitudinally extending coil with a plurality of tightly spaced turns. Thrombogenic fibers are positioned in the tightly spaced turns of the longitudinally extending coil to further attract thrombus thereto and quickly build up a mass that completely occludes the vessel.

To centrally position the embolization coil in substantial alignment with the longitudinal axis of the vessel lumen, the radially expanding turns of the conically helically shaped coil include spacing that increases proximally. This advantageously allows the embolization coil to be precisely and fixedly positioned at the occlusion site. The thrombogenic fibers positioned along the length of the coil and the proximally increasing turns also quickly build up a mass for occlusion of the vessel lumen.

For advantageously maintaining the conical helical shape of the coil, the continuous wire strand is stress relieved and, in particular, heat treated after the longitudinally extending coil is wound into a conical helical shape. The heat treatment advantageously relieves stresses that are formed when winding the longitudinally extending coil and the conically helically shaped coil. The heat treatment process includes heating the embolization coil at a stress relief temperature of the continuous wire strand for a first time period to relieve the residual stresses, and then gradually cooling down the coil from the stress relief temperature for a second time period greater than the first to minimize the introduction of new residual stresses during the cool down. Preferably, the continuous wire strand comprises a metallic alloy material, such as a platinum-tungsten alloy, that is substantially free of surface oxidation, which is considered a blood contaminant.

The conically helically shaped coil is formed by winding the longitudinally extending coil around a longitudinally tapered mandril with a plurality of minimally spaced turns. The mandril advantageously comprises a stainless steel material to minimize the formation of surface oxidation thereon during the heat treatment process. The metallic alloy material of the coil can also comprise at least one from a group consisting of platinum, stainless steel, iridium, palladium, tungsten, and gold. When wound around the tapered mandril, the coil is heated at the stress relief temperature of the metallic alloy and then cooled. The conically helically shaped coil is removed from the mandril, at which time the spacing between the radially expanding turns increases proximally from the distal end thereof. The embolization coil is then positioned in a cannula in which the coil is positioned therein in a delivery state for insertion into a guiding or delivery catheter.

3

Figure 1:
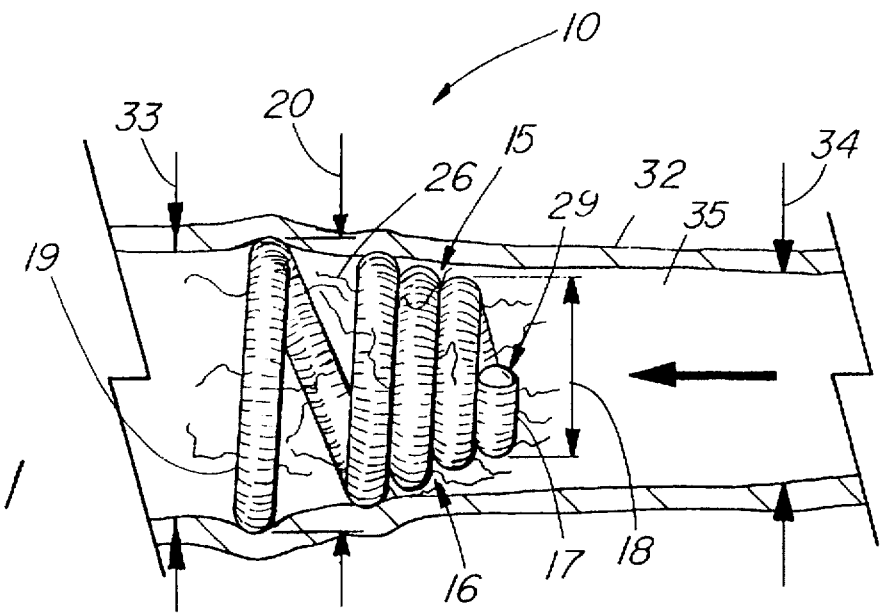
FIG. 1 depicts an illustrative conically helically shaped embolization coil of the present invention longitudinally positioned in the vessel of a patient.
Figure 2:
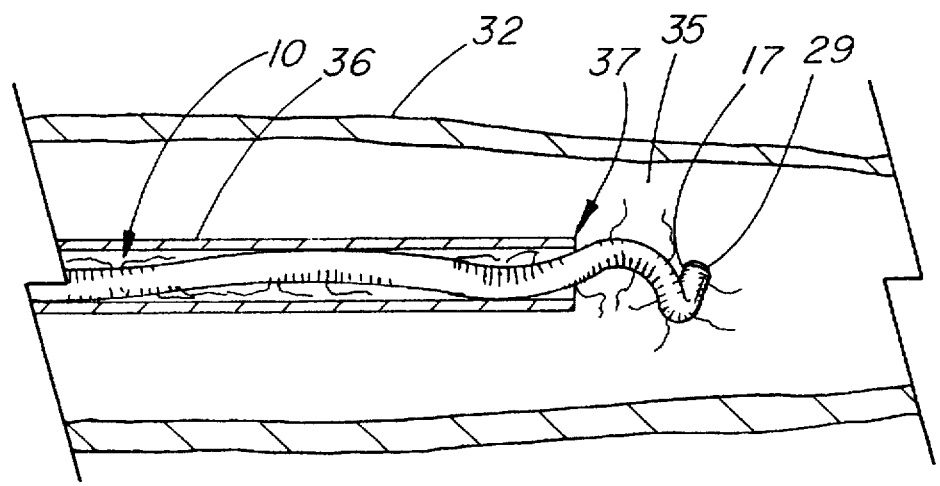
Figure 3:
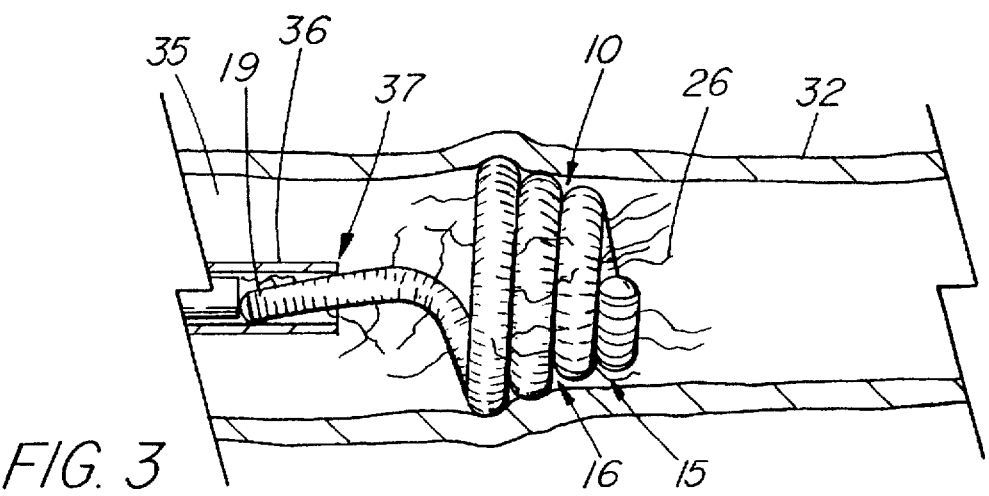
Figure 4:
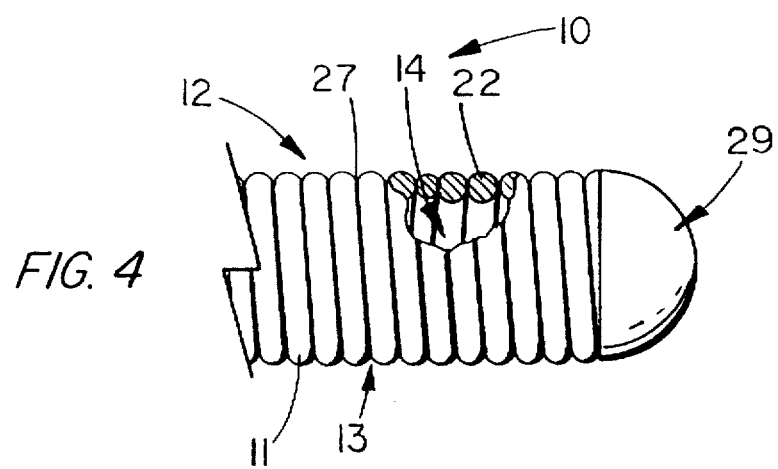
Figure 5:
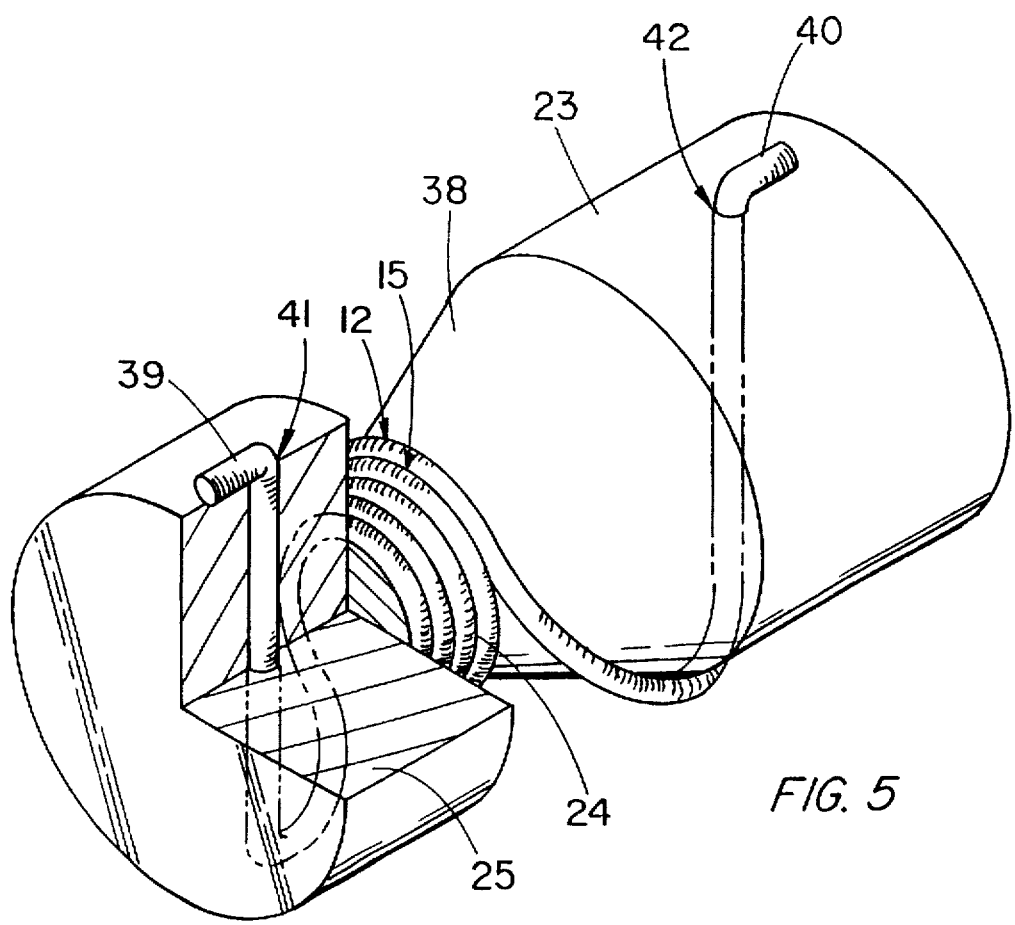
Figure 7:
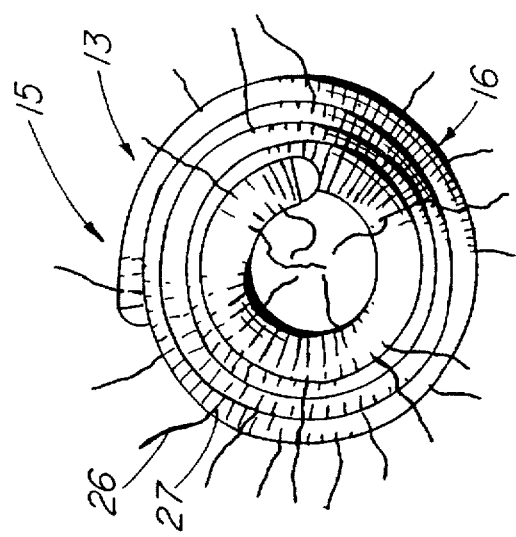
Figure 8:
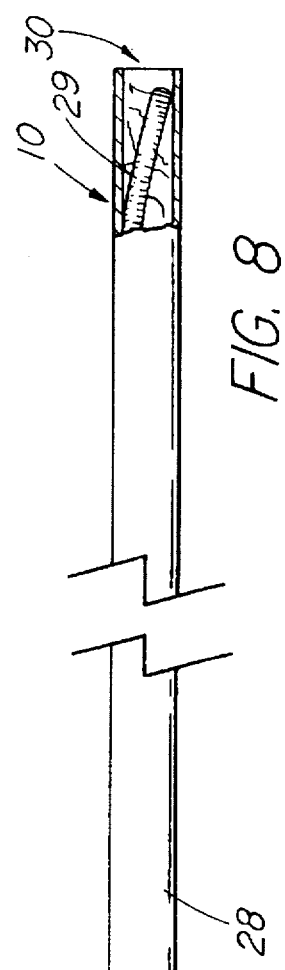
Figure 6:
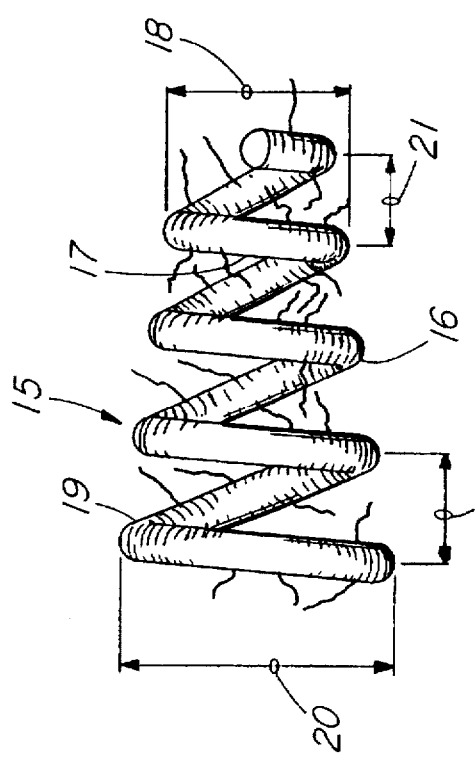

FIG. 2 depicts the distal turn of the embolization coil of FIG. 1 emerging from the distal end of a delivery catheter;

FIG. 3 depicts the embolization coil of FIG. 1 emerging from the distal end of a delivery catheter with only the proximal turn remaining in the delivery catheter;

FIG. 4 depicts a partially sectioned view of the embolization coil of FIG. 1 in an elongated condition prior to being wound into a conically helically shaped coil;

FIG. 5 depicts the longitudinally extending coil of FIG. 4 wound around the tapered surface of a mandril to form a conically helically shaped coil;

FIG. 6 depicts the conically helically shaped coil of FIG. 5 after it has been removed from the mandril;

FIG. 7 depicts an end view of the conically helically shaped coil of FIG. 6; and FIG. 8 depicts a partially sectioned view of a shipping cannula with the embolization coil of the present invention positioned therein.

DETAILED DESCRIPTION

FIG. 1 depicts illustrative embolization coil 10 longitudinally positioned in vessel 32 of a human or animal body. The embolization coil has been formed into conically helically shaped coil 15 having a longitudinal axis that is substantially aligned with the longitudinal axis of vessel 32. The conically helically shaped coil has a plurality of radially expanding turns 16 with thrombogenic fibers 26 spaced at predetermined intervals along the length of the coil. The conically helically shaped coil extends over almost the entire cross-sectional area of vessel lumen 35 to substantially impede blood flow and attract thrombus. The thrombogenic fibers of the embolization coil more readily attract thrombus to further build up a mass that entirely occludes the vessel.

Due to the build up of plaque and other irregularities in the vessel wall, lumen 35 has a maximum diameter 33 and a minimum diameter 34 through any given length of the vessel. To ensure longitudinal alignment and fixed positioning of the embolization coil in the vessel lumen, distal turn 17 of coil 15 has a minor diameter 18 that is less than minimum diameter 34 of the vessel, and compressed proximal turn 19 of coil 15, when in an uncompressed condition, has a major diameter 20 that is greater than maximum diameter 33 of the vessel. This sizing of the conically helically shaped coil ensures that distal end 29 of the coil is introduced from a delivery catheter into the central region of the vessel. The successive turns of the coil radially increase in size as the embolization coil is released from the delivery catheter to engage and expand against the interior surface or intimal layer of the vessel wall. As a result, minor diameter distal turn 17 does not engage the vessel wall and longitudinally displace the delivery catheter positioned at the occlusion site. The proximal radially expanding turns of the coil centrally and longitudinally position the coil in the vessel lumen. Furthermore, the most proximal turns of the coil readily expand against the interior surface of the vessel wall and fixedly position the coil at the desired occlusion site. Precision positioning of the coil is thus readily achieved without concern for the embolization coil emerging from the delivery catheter and tumbling or drifting to an undesired occlusion site in the vessel.

FIG. 2 depicts embolization coil 10 of FIG. 1 positioned in a stretched or loaded condition in delivery catheter 36 and distal end 29 of turn 17 of the coil emerging from distal end 37 of the catheter. Distal end 29 of the coil is centrally positioned in vessel lumen 35 with distal turn 17 emerging from the delivery catheter. As a result, distal end 29 of the coil as well as distal turn 17 is introduced into the vessel lumen without longitudinally displacing delivery catheter 36 from the occlusion site in vessel 32.

FIG. 3 depicts embolization coil 10 of FIG. 1 emerging from distal end 37 of delivery catheter 36 in vessel lumen 35 with only proximal turn 19 remaining in the delivery catheter. As shown, the proximal radially expanding turns 16 of conically helically shaped coil 15 have emerged from the delivery catheter and expanded to compress against the interior surface of the vessel wall. As a result, the longitudinal axis of the conically helically shaped coil is centrally positioned in vessel lumen 35 and aligned with the longitudinal axis of the vessel. Furthermore, the introduction of the embolization coil at the occlusion site is accomplished without longitudinally displacing the delivery catheter or allowing the coil to flow or tumble in the blood stream to an undesired occlusion site. Additionally, the radially expanding turns accurately and securely position the embolization coil at the occlusion site in the vessel. When the embolization coil is fully released from the delivery catheter, the radially expanding turns of the coil extend almost over the entire cross-sectional area of the vessel lumen. This significantly reduces blood flow and further promotes thrombus formation on the coil and thrombogenic fibers 26 extending from the coil.

FIG. 4 depicts a partially sectioned view of embolization coil 10 of FIG. 1 in an elongated condition prior to being wound into a conically helically shaped coil. The embolization coil comprises continuous wire strand 11 that has been wound in a well-known manner into longitudinally extending coil 12 with a plurality of tightly spaced turns 13 and hollow passage 14 extending longitudinally therein. Continuous wire strand 11 comprises a metallic alloy material 22 that is substantially free of surface oxidation that is considered an undesired contaminant in the bloodstream of a patient. Preferably, the continuous wire strand comprises a commercially available 0.003" diameter platinum wire with 8 percent tungsten. Other alternative alloys include well-known medical grade stainless steel along with alloys including at least one from a group consisting of platinum, iron, iridium, palladium, tungsten, and gold. These particular alloys exhibit extremely low levels of surface oxidation particularly when heat treated to relieve residual stresses formed during the winding of the embolization coil. Additionally, these metallic alloys are also considered thrombogenic to further promote thrombus formation and occlusion of the vessel at the occlusion site. The continuous wire strand is preferably wound into a longitudinally extending coil approximately 6 cm long with a 0.014" outside diameter and tightly spaced turns with minimal, if any, spacing 27 therebetween. Distal end 29 of the longitudinally extending coil is soldered or welded to present a rounded or smooth surface, which will not catch on the interior surface of the guiding catheter.

FIG. 5 depicts longitudinally extending coil 12 of FIG. 4 wound around longitudinally tapered surface 38 of mandril 23 to form conically helically shaped coil 15 with minimally spaced turns 24. Ends 39 and 40 of the longitudinally extending coil are positioned through respective transverse mandril holes 41 and 42 and bent to fixedly position the coil around longitudinally tapered surface 38. The outside diameter of mandril 23 preferably ranges from 0.250" to 0.325" with longitudinally tapered surface 38 necking down to a minimum diameter of 0.030" to 0.035". As a result, longitudinally tapered surface forms an angle with the longitudinal axis of the mandril of approximately 41 to 46 degrees.

Since the wire strand and mandril are heat treated, mandril 23 comprises material 25 such as stainless steel that is heat treated in an oxygen free oven or another metal such as titanium or a metallic alloy that exhibits extremely low levels of surface oxidation after being heat treated. As suggested, the stainless steel mandril is placed in an oxygen free oven such as a commercially available argon oven to minimize surface oxidation during the heat treatment process.

Longitudinally extending coil 12 wound around longitudinally tapered mandril 23 to form conically helically shaped coil 15 is stress relieved and, in particular, heat treated to relieve residual stresses that formed during winding of the embolization coil. In particular, these residual stresses are formed when continuous wire strand 11 is wound into longitudinally extending coil 12 and, more importantly, when longitudinally extending coil 12 is wound around tapered mandril 23 to form conically helically shaped coil 15. By way of example, the longitudinally extending coil 12 and tapered stainless steel mandril 23 are positioned in a commercially available argon oven to minimize the formation of surface oxidation particularly on the stainless steel mandril during the heat treatment process. The coil and mandril are heated in the oven to a stress relief temperature of the platinum-tungsten alloy of approximately 1,012 degrees Fahrenheit for a first time period of approximately 2 hours to relieve stresses formed during the winding of the coil. The heated coil and mandril are then cooled down from this stress relief temperature for a second time period of, for example, 8 hours, which is much greater than the first 2-hour time period. This gradual cool down period minimizes the formation of new residual stresses that can be formed when the coil is cooled down too quickly.

As was previously suggested, the material of the embolization coil as well as that of the mandril is selected to be substantially free of surface oxidation that can be readily formed during the heating and cooling of the coil and mandril in the oven. The formation of surface oxidation is a concern, since it is considered a contaminant when introduced into the bloodstream of a patient. After the coil and mandril are stress relieved, conically helically shaped coil 15 is removed from the mandril. Although the coil has been stress relieved and, in particular, heat treated, minimally spaced turns 24 of the coil on the mandril expand to a spacing that increases proximally from the distal end of the coil.

FIG. 6 depicts conically helically shaped coil 15 of FIG. 5 after it has been removed from the mandril. The conically helically shaped coil has a plurality of radially expanding turns 16 with spacing 21 that increases proximally from distal turn 17 to proximal turn 19. As previously indicated, distal turn 17 has minor diameter 18, whereas proximal turn 19 has major diameter 20. Spacing 21 between radially expanding turns 16 is typically no more than 2 mm in width at distal turn 17 and increases proximally to a maximum spacing of 5 mm at proximal turn 19.

FIG. 7 depicts an end view of conically helically shaped coil 15 of FIG. 6. Radially expanding turns 16 of the coil are readily observed from this end view. Thus, it can be more readily appreciated how the radially expanding turns of the embolization coil nearly cover the entire cross-sectional area of a vessel lumen. Thrombogenic fibers of, for example, commercially available 0.00075" diameter Z-twist, DACRON fiber material are placed at periodic intervals along the length of the coil in minimal spacing 27 between tightly spaced turns 13 of the longitudinally extending coil.

FIG. 8 depicts a partially sectioned view of shipping cannula 28 with embolization coil 10 inserted therein in a stretched condition. By way of example, the shipping cannula is a 21 gauge thin wall stainless steel tube with Luer-lock fitting 43 at the proximal end thereof. The embolization coil is positioned in this cannula for introduction into a guiding or delivery catheter for introduction at the occlusion site. Normally, the guiding or delivery catheter is percutaneously positioned at the occlusion site. The embolization coil is then transferred from the shipping cannula into the delivery catheter with an introducer stylet that is inserted through the proximal end of the shipping cannula and into the passage of the delivery catheter. To ensure proper placement of the embolization coil, distal end 29 of the embolization coil is positioned proximate distal end 30 of the shipping cannula with proximal end 31 positioned proximate the proximal end of the cannula.

It is to be understood that the above-described embolization coil is merely an illustrative embodiment of the principles of this invention and that other heat treated or stress relieved embolization coils may be devised by those skilled in the art without departing from the spirit and scope of this invention. Furthermore, other conically helically shaped coils with spacing that increases proximally between the radially expanding turns of the coil may also be devised by those skilled in the art without departing from the spirit and scope of the invention. Although the embolization coil has been stress relieved by way of a heat treatment process, other stress relieving treatment processes are contemplated, such as through mechanical, chemical, or electrical processes.

What is claimed is:

1. An embolization coil (10) comprising:
a continuous wire strand (11) wound into a longitudinally extending coil (12) having a plurality of tightly spaced turns (13), said longitudinally extending coil wound into a conically helically shaped coil (15) having a plurality of radially expanding turns (16), said radially expanding turns longitudinally overlapping each other, whereby said radially expanding turns longitudinally contact each other in response to blood flowing therethrough to occlude a vessel in which the embolization coil is positioned.

2. The embolization coil of claim 1 wherein said radially expanding turns include spacing (21) therebetween that increases proximally.

3. The embolization coil of claim 1 wherein said conically helically shaped coil is heat treated to relieve stresses that are formed when winding said longitudinally extending coil and said conically helically shaped coil.

4. The embolization coil of claim 1 wherein said continuous wire strand is comprised of a metallic alloy and wherein conically helically shaped coil is formed by the steps of: winding said longitudinally extending coil around a longitudinally tapered mandril (23) with a plurality of minimally spaced turns (24), heating said conically helically shaped coil when wound around said longitudinally tapered mandril at a stress relief temperature of said metallic alloy for a first time period, and cooling said conically helically shaped coil when wound around said longitudinally tapered mandril from said stress relief temperature for a second time period greater than said first time period.

5. The embolization coil of claim 4 wherein the steps of forming said conically helically shaped coil further include selecting said longitudinally tapered mandril of a material (25) that remains substantially free of surface oxidation during heating and cooling of said conically helically shaped coil.

6. The embolization coil of claim 5 wherein said metallic alloy comprises at least one from a group consisting of platinum, stainless steel, iridium, palladium, tungsten, and gold.

7. The embolization coil of claim 1 wherein said conically helically shaped coil is heated at a stress relief temperature of said continuous wire strand for a first time period and then gradually cooled down from said stress relief temperature for a second time period greater than said first time period.

8. The embolization coil of claim 1 wherein said continuous wire strand comprises a metallic material (22) that is substantially free of surface oxidation.

9. The embolization coil of claim 1 further comprising thrombogenic fibers (26) positioned in said plurality of tightly spaced turns of said longitudinally extending coil.

10. An embolization coil (10) comprising:

a continuous wire strand (11) of a metallic alloy (22) wound into a longitudinally extending coil (12) having a plurality of tightly spaced turns (13), said longitudinally extending coil wound into a conically helically shaped coil (15) having a plurality of radially expanding turns, said conically helically shaped coil of said metallic alloy being stress relieved and substantially free of surface oxidation, said radially expanding turns longitudinally overlapping each other, whereby said radially expanding turns longitudinally contact each other in response to blood flowing therethrough to occlude a vessel in which the embolization coil is positioned.

11. The embolization coil of claim 10 wherein a distal turn (17) of said radially expanding turns has a minor diameter (18) less than a major diameter (20) of a proximal turn (19) of said radially expanding turns, said major diameter (20) being no greater than 30 mm.

12. The embolization coil of claim 10 wherein said radially expanding turns have a spacing (21) therebetween that increases from a distal turn (17) to a proximal turn (19) thereof.

13. The embolization coil of claim 10 wherein said conically helically shaped coil is formed by the steps of: winding said longitudinally extending coil around a longitudinally tapered mandril (23) with a plurality of minimally spaced turns (24) and heat treating said conically helically shaped coil when wound around said longitudinally tapered mandril to relieve residual stresses formed therein.

14. The embolization coil of claim 10 wherein said metallic alloy includes at least one from a group consisting of platinum, stainless steel, iridium, palladium, tungsten, and gold.

15. The embolization coil of claim 14 wherein said conically helically shaped coil is formed by the steps of: winding said longitudinally extending coil around a longitudinally tapered mandril (23) and heating said conically helically shaped coil at a stress relief temperature of said metallic alloy for a first time period and then cooling said conically helically shaped coil down from said stress relief temperature for a second time period greater than said first time period.

16. The embolization coil of claim 10 further comprising thrombogenic fibers (26) positioned in said tightly spaced turns at predetermined intervals therealong.

17. The embolization coil of claim 10 further comprising a cannula (28) having a passage extending longitudinally therethrough and in which said conically helically shaped coil is positioned therein.

18. The embolization coil of claim 17 wherein a distal end (29) of said conically helically shaped coil is positioned proximate a distal end (30) of said cannula and wherein a proximal end (31) of said conically helically shaped coil is positioned proximally from said distal end thereof in said cannula.

19. An embolization coil (10) comprising:

a continuous wire strand (11) of a platinum-tungsten alloy (22) that is substantially free of surface oxidation, said strand wound into a longitudinally extending coil (12) having a plurality of tightly spaced turns (13), said longitudinally extending coil wound into a conically helically shaped coil (13) having a plurality of radially expanding turns (16), a distal turn (17) of said radially expanding turns having a minor diameter (18) less than a major diameter (20) of a proximal turn (19) of said radially expanding turns, said major diameter (20) being no greater than 30 mm, said radially expanding turns longitudinally overlapping each other and including proximally increasing spacing (21) from said distal turn to said proximal turn, said conically helically shaped coil of said platinum-tungsten alloy being formed and stress relieved by the steps of: winding said longitudinally extending coil around a longitudinally tapered mandril (23) with a plurality of minimally spaced turns (24), heating said conically helically shaped coil for a first time period at a stress relief temperature of said platinum-tungsten alloy to relieve stresses formed therein, and then cooling said conically helically shaped coil down from said stress relief temperature over a second time period greater than said first time period to minimize formation of new residual stresses therein; and thrombogenic fibers (26) positioned in said plurality of tightly spaced turns, selected of said radially expanding turns being positionable within an other thereof, whereby said radially expanding turns longitudinally contact each other in response to blood flowing therethrough to occlude a vessel in which the embolization coil is positioned.

\* \* \* \* \*